(12) United States Patent
Kumosani et al.

(10) Patent No.: US 9,855,209 B1
(45) Date of Patent: Jan. 2, 2018

(54) ANTI-BACTERIAL MOUTHWASH

(71) Applicant: KING ABDULAZIZ UNIVERSITY, Jeddah (SA)

(72) Inventors: Taha Kumosani, Jeddah (SA); Elie K. Barbour, Jeddah (SA); Werner Krull, Luzern (DE)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 0 days.

(21) Appl. No.: 15/414,988

(22) Filed: Jan. 25, 2017

(51) Int. Cl.
 *A61K 8/97* (2017.01)
 *A61K 8/92* (2006.01)
 *A61K 8/60* (2006.01)
 *A61Q 11/00* (2006.01)

(52) U.S. Cl.
 CPC ............... *A61K 8/97* (2013.01); *A61K 8/608* (2013.01); *A61K 8/922* (2013.01); *A61Q 11/00* (2013.01); *A61K 2800/30* (2013.01); *A61K 2800/74* (2013.01); *A61K 2800/92* (2013.01)

(58) Field of Classification Search
 None
 See application file for complete search history.

(56) References Cited

U.S. PATENT DOCUMENTS

| | | | |
|---|---|---|---|
| 4,150,151 A | | 4/1979 | Pader et al. |
| 2006/0088616 A1 * | | 4/2006 | Seiberg ............ A61K 8/97 424/769 |
| 2008/0247972 A1 | | 10/2008 | Conceicao |
| 2012/0237455 A1 * | | 9/2012 | Trivedi ............ A61K 8/97 424/48 |

FOREIGN PATENT DOCUMENTS

| FR | 2814070 A1 * | 3/2002 | ............ A61K 8/97 |
|---|---|---|---|
| JP | 0413630 A * | 1/1992 | |

OTHER PUBLICATIONS

R. Karousou. The Sage Plants in Greece. Chapter II.2 of Sage: The Genus Salvia, ed by S.E. Kintzios. Taylor and Francis, 2000, pp. 37 and 38.*

* cited by examiner

*Primary Examiner* — Frederick Krass
*Assistant Examiner* — Michael P Cohen
(74) *Attorney, Agent, or Firm* — Richard C. Litman

(57) ABSTRACT

An anti-bacterial mouthwash includes aqueous extracts of *Salvia libanotica* and *Malva sylvestris* plants, at least one essential oil, and an emulsifier. The essential oil can include at least one of *eucalyptus* oil and peppermint oil. The emulsifier can include polyoxyethylene sorbitan. The anti-bacterial mouthwash can be free from alcohol.

7 Claims, No Drawings

ANTI-BACTERIAL MOUTHWASH

1. FIELD OF THE INVENTION

The present invention relates generally to mouthwash formulations, and particularly to mouthwash formulations including aqueous extracts of *Salvia libanotica* and *Malva sylvestris* plant

2. DESCRIPTION OF THE RELATED ART

Mouthwash is generally used to reduce or prevent bad breath, suppress oral microbiota colonization, and control tooth decay and gum disease. Conventional mouthwashes have always contained fairly high levels of alcohol with percentages ranging from approximately 10% up to about 30% by volume. Alcohol is used both as a disinfectant and as a solvent in which other additives such as astringents, fluorides, color additives, flavor oils, bactericidal actives and the like can be dissolved and then dispersed into solution. High levels of alcohol are generally used to provide a disinfection function since lower concentrations are sufficient to dissolve and disperse the various components into solution. Alcohol also provides a preservative role for the mouthwash during storage and use as well as enhancement of flavor oil organoleptic cues.

There is a substantial need for the development of a reduced alcohol or alcohol-free mouthwash within which essential oils are completely dissolved. Also there is a need to develop mouthwash compositions that facilitate the consumer's daily care for oral hygiene to elongate the life of the teeth, maintain the health of the gum, and provide a socially-acceptable smell of breath.

Thus, a mouthwash solving the aforementioned problems is desired.

SUMMARY OF THE INVENTION

An anti-bacterial mouthwash includes aqueous extracts of *Salvia libanotica* and *Malva sylvestris* plants, at least one essential oil, and an emulsifier. The essential oil can include at least one of eucalyptus oil and peppermint oil. The emulsifier can include polyoxyethylene sorbitan. The anti-bacterial mouthwash can be free from alcohol. The anti-bacterial mouthwash can include about 98% (V/V) water extract of *Salvia libanotica* and *Malva sylvestris*, about 0.4% (V/V) essential oil, and about 1.6% (V/V) emulsifier.

A method of reducing bacteria in the mouth of a patient includes rinsing the oral cavity of the patient with the anti-bacterial mouthwash for a time sufficient to reduce the concentration of bacteria in the mouth. The bacteria can include *Streptococcus mutans*.

These and other features of the present invention will become readily apparent upon further review of the following specification and drawings.

DETAILED DESCRIPTION OF THE PREFERRED EMBODIMENTS

An anti-bacterial mouthwash includes aqueous extracts of *Salvia libanotica* and *Malva sylvestris* plants, at least one essential oil, and an emulsifier. The essential oil can include at least one of eucalyptus oil and peppermint oil. The emulsifier can include polyoxyethylene sorbitan. The anti-bacterial mouthwash can be free from alcohol. A percent composition (V/V) of the anti-bacterial mouthwash can include about 98% water extract of *Salvia libanotica* and *Malva sylvestris*, about 0.4% essential oil (e.g., 0.2% eucalyptus oil and 0.2% peppermint oil), and about 1.6% emulsifier. The water extract can be prepared using equal weights of the *Salvia libanotica* and *Malva sylvestris* plants, e.g., leaves of the plants. The anti-bacterial mouthwash can have a pH of about 5.0 to about 6.0. The mouthwash can include flavor oils at concentrations ranging from 0.1% w/v to 3.0% w/v. The flavor oils can include at least one of orange flower oil, cinnamon oil, lemongrass oil, anise oil and vanillin oil.

It is believed that the antimicrobial activity of the anti-bacterial mouthwash can be attributed to the essential oils and the ingredients present in the water extract of *Salvia libanotica*, while the emollient effect on the mucosal layer of the mouth and the anti-inflammatory effects can be attributed to the ingredients in the water extract of *Malva sylvestris*, namely, the mucilage, flavonoids, and fatty acid compositions. The main ingredient of eucalyptus oil is the 1,8-cineol (0.160%), while the main ingredients of the peppermint oil are the menthol (0.08%) and menthone (0.04-0.09%). The minor ingredients of the eucalyptus oil include pinene $(2.0\text{-}20.0) \times 10\text{-}3\%$, phellandrine $(2.0\text{-}20.0) \times 10\text{-}3\%$, limonene $(2.0\text{-}20.0) \times 10\text{-}3\%$, and y-terpinene $(2.0\text{-}20.0) \times 10\text{-}3\%$. The minor ingredients of the peppermint oil include methylacetate $(5.0\text{-}20.0) \times 10\text{-}3\%$ and methofuran $(5.0\text{-}20.0) \times 10\text{-}3\%$.

The main active ingredients of the water extract of the leaves of *Salvia libanotica* include Phenols, 0.056%; flavonoids, 0.040%. The main active ingredients of the water extract of the leaves of *Malva sylvestris* include Phenols, 0.038% and flavonoids, 0.021%.

The food grade emulsifier, polyoxyethylene sorbitan, can create a homogeneous dispersion of the ingredients that are present in both the water extract and the essential oils, resulting in similar ameliorating effects at each point of the oral tissues. The emulsifier is acceptable as a food additive, and its incorporation in the anti-bacterial mouthwash can be in amounts of about 0.1 to 8.0% and preferably between about 1.6 to about 2.0%, based on the acceptable daily intake of to 25 mg of this emulsifier in food, as suggested by WHO in 1974. The mouthwash can be free from artificial flavors, due to the acceptable natural flavors present in both the water extract and the essential oils. The pH of the preparation can be adjusted by the buffer of sodium bicarbonate, or citrate and its citric acid, to reach to a pH of about 5.0 to about 6.0, at which the synergism in bioactivity of ingredients of the mouthwash is optimized. The anti-bacterial mouthwash can include flavor oils at concentrations of 0.1-3.0% w/v. A blend of these flavors could be formed from the oil of orange flowers, cinnamon, and lemongrass. Different combinations of these three flavor oils can be used, each from 0.03-1.3% w/v. Once the flavor oils are blended, they can be incorporated in the mouthwash at a preferable range of 0.35% to 1.0%. Additional flavors can be included, such as those of anise and vanillin. Safe softeners, including glycerin, can be present in the mouthwash at a wide range of about 0.5%-15.5%, preferably at 6.5%. Different approved dyes can be added (yellow, blue, or green) at about $2.0 \times 10\text{-}4\text{-}6.0 \times 10\text{-}4$ (w/v) and preferably at $3.5 \times 10\text{-}4$ (w/v).

A method of using the anti-bacterial mouthwash can include the rinsing the oral cavity of a patient with the anti-bacterial mouthwash for a time sufficient to reduce the concentration of bacteria in the mouth. The bacteria can include *Streptococcus mutans*, but is not limited thereto and could include other bacteria commonly found in the oral cavity.

The present technology, thus generally described, will be understood more readily by reference to the following examples, which is provided by way of illustration and is not intended to limit the scope of the present technology.

Example 1

Preparation of the Anti-Bacterial Mouthwash

About 98 Kg of water extract of equivalent amounts of *Salvia libanotica* and *Malva sylvestris* (1/5 wt./volume) was added over 68 Kg of glycerin and 1.0 Kg of sodium bicarbonate, mixed well and left to clear, forming a mixture, referred to herein as "M1." In a separate container, about 200 g of peppermint oil and 200 g of *eucalyptus* oil were added over 1.6 Kg of polyoxyethylene sorbitan, mixed well and left to clear, forming a mixture referred to herein as "M2." The M1 was added slowly over the M2, followed by mixing for 45 minutes. Sterile water was added to a total volume of 100 liters and the pH was adjusted to 5.5 by the use of acid or base, depending on the pH of the final mixture.

The % weight/volume of ingredients in the resulting anti-bacterial mouthwash preparation of 100 liters was: 1. 1,8-cineol 0.160%, 160 g/100 liters; 2. Menthol 0.080%, 80 g/100 liters; 3. Menthone 0.063%, 63 g/100 liters; 4. Pinene 0.012%, 12 g/100 liters; 5. Phellandrine 0.014%, 14 g/100 liters; 6. Limonene 0.015%, 15 g/100 liters; 7. Y-Terpinene 0.011%, 11 g/100 liters; 8. Methyl acetate 0.014%, 14 g/100 liters; 9. Methofuran 0.06%, 60 g/100 liters; 10. Phenols of *Salvia libanotica* 0.056%, 56 g/100 liters; 11. Flavonoids of *Salvia Libanotica* 0.040%, 40 g/100 liters 12. Phenols of *Malva* sylvestris 0.038%, 38 g/100 liter; 13. Flavonoids of *Malva* sylvestris 0.021%, 21 g/100 liters 14. Glycerin (99% grade) 6.8%, 6.8 Kg/100 liters; 15. Polyoxyethylene sorbitan 1.6%, 1.6 Kg/100 liters; 16. Sodium bicarbonate 1.0% 1.0 Kg/100 liters.

Example 2

Anti-Bacterial Effects of Using the Anti-Bacterial Mouthwash

The first experimental design, targeting the evaluation of the antimicrobial effect of the inventive mouthwash, included four groups of people (20 subjects/group), of ages between 20-22 years and an average ratio of girls to boys equivalent to 1.2:1.0. Each group was included in the experiment at a different time. The sputum of each person was collected before and after the use of the inventive mouthwash in 25 ml volume and a contact time of 1 min. A serial dilution of the sputum of every individual was performed, in which each dilution was plated in 0.1 ml inocula onto duplicates of Nutrient Agar plates and incubated aerobically at 37° C. for 48 hrs. Plates resulting in colony forming units between 30-300 were included in calculation of the bacterial count per milliliter of sputum. The percent reduction in the mean oral microbiota count of each group was determined.

The mean oral aerobic and facultative microbiota counts in the sputum, before and after 1 minute contact time of 25 ml of the anti-bacterial mouthwash per subject, are presented in Table 1. The mean oral microbiota counts, per one milliliter of sputum, after rinsing with the anti-bacterial mouthwash (4 trials, around 20 subjects/each) was consistently and significantly lower than that before the rinse ($P<0.05$), with the mean of the mean % of oral bacterial count of all four trials equaling 42.1%.

TABLE 1

| Trial No. | Cases | Mean oral microbiota count (CFU/ml Sputum) | | Mean % Reduction of Count |
|---|---|---|---|---|
| | | Before wash | After Wash | |
| 1 | 22 | $(7.44 \times 10^3)^a$ | $(5.27 \times 10^3)^b$ | 29.2 |
| 2 | 20 | $(7.86 \times 10^3)^a$ | $(4.15 \times 10^3)^b$ | 47.2 |
| 3 | 19 | $(8.03 \times 10^3)^a$ | $(4.40 \times 10^3)^b$ | 45.3 |
| 4 | 21 | $(7.68 \times 10^3)^a$ | $(4.10 \times 10^3)^b$ | 46.6 |
| Mean of Mean % reduction | | | | 42.1 |

[a,b]Mean oral microbiota count followed by different alphabet superscripts are significantly different at $P < 0.05$.

Example 3

Evaluation of the Mouthwash Against *Streptococcus mutans*

This second experimental design, targeting the reduction of *Streptococcus mutans* by the anti-bacterial mouthwash, had two different treatments, namely oral rinsing with the anti-bacterial mouthwash versus the rinse of control subjects' mouths with sterile saline, including 20 subjects/each of the two treatments. The procedure of oral washing, sputum sampling, and sputum-serial dilution was similar to that followed by the subjects included in the first experimental design. The dilutions were plated in duplicate onto Trypticase Yeast-Extract Cystine Sucrose Bacitracin agar plates, and incubated at 37° C. for a period of 5 days, under the atmospheric conditions of 91% $N_2$, 5% $CO_2$, and 4% $H_2$ (Van Palenstein Helderman et al., 1983; Schaeken et al., 1986). The percent reduction in mean count of *Streptococcus mutans* in each of the two treatments was calculated.

The mean percent reduction in *Streptococcus mutans* count per milliliter of sputum, in the two groups that were respectively treated with the anti-bacterial mouthwash versus saline, is shown in Table 2. The respective mean percent reductions in *S. mutans* of the two treatments were significantly different, in which the anti-bacterial mouthwash reduced the *Streptococcus mutans* by a mean of 65.2% compared to the mean reduction of 3.25 obtained by the control subjects that had a mouth rinse with sterile saline ($P<0.05$). Table 2 displays the mean percentage reduction in *Streptococcus mutans* count per milliliter of saliva following treatment by the anti-bacterial mouthwash versus sterile saline (20 subjects/treatment).

TABLE 2

| Mouthwash | No. cases | Mean oral *S. mutans* count (CFU/ml sputum) | | Mean % reduction in *S. mutans* count |
|---|---|---|---|---|
| | | Before Wash | After Wash | |
| Anti-bacterial mouthwash | 20 | $(5.20 \times 10^3)^a$ | $(1.81 \times 10^3)^b$ | 65.2[1] |
| Sterile saline | 20 | $(5.43 \times 10^3)^a$ | $(5.26 \times 10^3)^a$ | 3.2[2] |

[a,b]Means in a row followed by different alphabet superscripts are significantly different ($P < 0.05$);
[1,2]Means in a column followed by different Arabic superscripts are significantly different

Example 4

Rabbit-Draize Eye Test

The safety of the anti-bacterial mouthwash in its inability to cause inflammatory reactions was tested by the Rabbit- Draize Eye Test, a test adopted by the Food and Drug Administration (Draize et al., 1944). Briefly, 9 rabbits of one year old were divided into three groups (3 rabbits/group). Rabbits of Group 1 were the controls, deprived of any application of materials on the eyes, while rabbits of Group 2 received the same dilution of the mouthwash used in mouth rinsing experiments at 0.05 ml/each of their left eye, repeating the application for three consecutive days. Rabbits of Group 3 received three times the concentration of the anti-bacterial mouthwash that is used in mouth rinse experiments (3×), with same application volume per eye and repetitions as that followed in Group 2. The right and left eyes of the 9 rabbits were examined daily and for a period of 7 days, effective the first day of applications. The eye examination included the observation for redness, swelling, discharge, ulceration, hemorrhaging, cloudiness, or blindness. The three days of ocular application of the anti-bacterial mouthwash, on the rabbits left eyes at two different concentrations (1× and 3×), resulted in absence of gross lesions, similar to that observed in the external-control group and in the internal-control right eyes of the rabbits receiving the mouthwash in the left eye as shown in Table 3. Table 3 shows the Draize Eye Test assessment of the anti-bacterial mouthwash on the left eyes of experimental rabbits administered the same concentration used in the mouthwash experiments of human subjects (Example 2) (1×) and other rabbits receiving three times that concentration (3×) in comparison to controls with application of sterile saline in the left eyes. Three applications for three consecutive days (0.05 ml/left eye) of the three rabbit groups were treated respectively with saline, anti-bacterial mouthwash (1×), and anti-bacterial mouthwash (3×) respectively. Each group of rabbits included three rabbits.

TABLE 3

Presence of Gross Lesions in Left and Right Eyes

| Treatment | Left Eye | Right Eye |
|---|---|---|
| Saline | None | None |
| Mouthwash (1X) | None | None |
| Mouthwash (3X) | None | None |

Observations for gross lesions in both eyes started from the first day of application and through 4 days post the last application. The eyes were observed for redness, swelling, discharge, ulceration, hemorrhaging, cloudiness and blindness.

Example 5

Ames Test

The Ames test was followed according to a previously reported procedure (Ames et al, 1973; Mortelmans and Zeiger, 2000). Briefly, the test organism *Salmonella enterica* subsp. *Enterica serovar Typhimurium* (ATCC® 29629-Strain Designations: TA 1535), an auxotrophic mutant, was provided by ATCC, Manassas, USA. This auxotrophic isolate requires histidine for its growth, due to a mutation in its DNA. Substances to be tested for their mutagenesis, could be added in the histidine-free medium of the test organism, to monitor their ability to reverse back the mutated *Salmonella typhimurium* to a prototrophic state, enabling it to grow. The anti-bacterial mouthwash was incorporated in the histidine-free medium used in the Ames test, at four different concentrations namely, 1/100×, 1×, 1.5×, and 2× (where X is the dilution used in mouth rinsing experiments), while another batch of the medium was deprived of the Mouthwash substance. Ethidium bromide, an expected positive inducer of mutations in the test organism, was incorporated in another batch of the same histidine-free medium at two concentrations namely, 20 and 200 nmole. The *S. Typhimurium* was cultured in triplicate onto the 4 differently supplemented media, and on the 5th control medium that was deprived of supplementation, to observe the growth of this test organism. The bacterium was spread over these media with small amounts of histidine that helps in the initiation of the growth, and once this amino acid is depleted, only the mutated cells by the supplemented substance will be able to synthesize their histidine, and to continue their growth. Thus, mutagenicity is determined in this research from the proportion of the average colony forming units formed on triplicate of the supplemented medium with the anti-bacterial mouthwash versus that formed on triplicate of the non-supplemented medium, with the growth on Ethidium bromide acting as a positive control of the test.

The results of the Ames test in relation to reversion of the *S. Typhimurium* test organism from its auxotrophic to prototrophic nature is shown in Table 4. The incorporation of the mouthwash at 1/100×, 1.0×, 1.5×, and 2.0×% in the histidine-free medium of the grown *S. Typhimurium* resulted in statistically non-significant difference in its count compared to that obtained on the same medium supplemented with minimum histidine (P>0.05). The ethidium bromide supplementation in the medium at 20 and 200 nmol level resulted in a respective % increase in colony count compared to growth on the minimal histidine-supplemented medium equivalent to 0 and 12.5%, an apparent reversion of mutation in the *S. Typhimurium* at a concentration of ethidium bromide equivalent to 200 nmol, helping it to synthesize its own histidine (P<0.05).

TABLE 4

| Supplementation Of Medium With anti-bacterial mouthwash[2] and control substance | Mean % increase in *S. Typhimurium* CFU[1] count of triplicate relative to mean triplicate count on minimal Histidine-supplemented medium |
|---|---|
| His- | −180.0 |
| X/100 | −16.7 |
| 1X | −7.7 |
| 1.5X | 0.0 |
| 2.0X | −16.7 |
| Eth[3] 20 nmol/plate | 0.0 |
| Eth 200 nmol/plate | 12.5 |

[1]CFU stands for Colony Forming Units
[2]Mouthwash is supplemented at different concentrations of X/100, 1X, 1.5X, and 2.0X, in which X is the dilution used in mouth rinsing experiments.
[3]Eth stands for Ethidium bromide used as positive control for induction of mutation in the *S. Typhimurium* allowing it to synthesize its own histidine, enabling it to increase its count on the histidine free medium.

The anti-microbial mouthwash exhibits anti-bacterial activity, an emollient effect on the mucosal layer of the mouth, as well as anti-inflammatory effects.

It is to be understood that the present invention is not limited to the embodiments described above, but encompasses any and all embodiments within the scope of the following claims.

We claim:

1. An alcohol-free anti-bacterial mouthwash, consisting of:
   an aqueous extract of *Salvia libanotica* and *Malva sylvestris* in an amount of about 98%; about 0.4% of essential oil; and an emulsifier in an amount of about 1.6%.

2. The anti-bacterial mouthwash according to claim 1, wherein said essential oil includes at least one of *eucalyptus* oil and peppermint oil.

3. The anti-bacterial mouthwash according to claim 1, wherein the emulsifier is polyoxyethylene sorbitan.

4. The anti-bacterial mouthwash according to claim 1, wherein a plant weight/water volume ratio of the water extract of *Salvia libanotica* and *Malva sylvestris* is 1/5.

5. The anti-bacterial mouthwash according to claim 1, wherein the mouthwash has a pH of about 5.0 to about 6.0.

6. A method of reducing bacteria in the mouth of a patient, said method comprising:
- rinsing the oral cavity of a patient with the anti-bacterial mouthwash according to claim 1 for a period of time sufficient to reduce a concentration of bacteria in the mouth.

7. The method of claim 6, wherein the bacteria is *Streptococcus mutans*.

* * * * *